United States Patent
Kimm et al.

(10) Patent No.: US 10,183,130 B2
(45) Date of Patent: Jan. 22, 2019

(54) MEASURING VALVE HEALTH BY PRESSURE MONITORING

(71) Applicant: CareFusion 303, Inc., San Diego, CA (US)

(72) Inventors: Daniel Kimm, San Diego, CA (US); Lee Good, San Diego, CA (US); Alexander Ellington, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 370 days.

(21) Appl. No.: 14/699,974

(22) Filed: Apr. 29, 2015

(65) Prior Publication Data

US 2016/0317762 A1    Nov. 3, 2016

(51) Int. Cl.
| | | |
|---|---|---|
| *A61M 5/50* | (2006.01) |
| *A61M 5/168* | (2006.01) |
| *F16K 37/00* | (2006.01) |
| *A61M 5/142* | (2006.01) |
| *A61M 39/22* | (2006.01) |

(52) U.S. Cl.
CPC ...... *A61M 5/5086* (2013.01); *A61M 5/14216* (2013.01); *A61M 5/16813* (2013.01); *A61M 5/16854* (2013.01); *A61M 5/16881* (2013.01); *F16K 37/00* (2013.01); *A61M 39/22* (2013.01); *A61M 2205/3331* (2013.01); *A61M 2205/581* (2013.01); *A61M 2205/582* (2013.01)

(58) Field of Classification Search
CPC .......... A61M 5/16813; A61M 5/16854; A61M 5/16859; A61M 5/16881; A61M 5/5086; A61M 5/14216; A61M 2205/3331; A61M 2205/3341; A61M 2205/3351; A61M 2205/3355; A61M 2005/16863; A61M 2005/16868; A61M 2005/16872; A61M 5/142; A61M 2205/50; F16K 37/0075; F16K 37/0083; F16K 37/0091
See application file for complete search history.

(56) References Cited

U.S. PATENT DOCUMENTS

| | | | |
|---|---|---|---|
| 5,695,473 A | 12/1997 | Olsen | |
| 5,935,099 A | 8/1999 | Peterson et al. | |
| 7,255,680 B1 | 8/2007 | Gharib | |
| 2009/0221986 A1* | 9/2009 | Wang ................ | A61M 5/16877 604/503 |
| 2011/0060758 A1 | 3/2011 | Schlotterbeck et al. | |
| 2014/0330205 A1 | 11/2014 | Tian | |
| 2016/0151560 A1 | 6/2016 | Toro et al. | |

FOREIGN PATENT DOCUMENTS

WO    WO-2004/035116 A1    4/2004

* cited by examiner

*Primary Examiner* — Theodore Stigell
*Assistant Examiner* — James D Ponton
(74) *Attorney, Agent, or Firm* — Mintz Levin Cohn Ferris Glovsky and Popeo, P.C.

(57) ABSTRACT

A medical fluid infusion system includes a pump system configured to deliver a fluid drug to a patient. The system includes a pump, such as a piston pump, for driving fluid to a patient. One or more pressure sensors are configured to measure and detect changes in fluid pressure in a fluid flow line of the infusion system. The changes in fluid pressure, when detected, can be an indication of proper or improper functioning of a valve system of the pump system of the fluid infusion system.

21 Claims, 2 Drawing Sheets

MEASURING VALVE HEALTH BY PRESSURE MONITORING

BACKGROUND

Intravenous (IV) fluid delivery pumps are used to deliver fluid to a patient or to draw out fluid from a patient's body wherein the patient can be a human or animal. A delivery pump may be, for example, a piston-type pump that drives fluid by moving a piston up-and-down relative to fluid contained in a piston chamber. The pump may further include valve actuators on either side of the piston. The piston and the valve actuators may interface with the piston chamber and inlet-side and outlet-side valves on a disposable cassette. The upward stroke of the piston movement creates a pressure differential that forces fluid out of the piston chamber toward the patient.

Such pumps typically include one or more pressure sensors that measure fluid pressure along a fluid pathway. The valves on the disposable selectively control the flow of fluid into and out of the piston chamber. The valves and the actuators that engage therewith are critical components that are subject to wear and failure. The failure of such valves or actuators can result in large flow rate errors, which can be harmful for a patient, and can also result in other problems related to the delivery of fluid to the patient.

Current systems do not provide for the monitoring of proper valve or actuator function. In view of the foregoing, there is a need for improved systems and devices for monitoring proper valve function in a drug infusion piston pump.

SUMMARY

Described herein is a medical fluid infusion system including a pump system configured to deliver a fluid drug to a patient. The system includes a pump, such as a piston pump, for driving fluid to a patient. One or more pressure sensors are configured to measure and detect changes in fluid pressure in a fluid flow line of the infusion system. The changes in fluid pressure, when detected, can be an indication of proper or improper functioning of a valve system of the pump system of the fluid infusion system.

In one aspect, there is disclosed a fluid infusion system for delivery of a fluid medicant to a patient, comprising: a fluid line through which fluid flows toward the patient; a first valve position along the fluid line, wherein the first valve opens to permit fluid flow through the fluid line and closes to prohibit fluid flow through the fluid line; a first pressure sensor positioned along the fluid line, wherein the first pressure sensor measures fluid pressure at a location in the fluid line near the first valve; and a processor coupled to the first pressure sensor, wherein the processor is configured to detect an occurrence of a fluid pressure spike at the first valve, and wherein the processor is configured to compare data associated with the fluid pressure spike to predetermined criteria in order to determine whether the first valve is functioning properly, and wherein the processor emits a signal indicative of whether the first valve is functioning properly.

In another aspect, there is disclosed method of detecting a condition of a valve system in a fluid infusion system with a valve actuator that moves from occluding to non-occluding positions, comprising: detecting a change in fluid pressure that occurs in the fluid line when the valve actuator moves from a non-occluding position to an occluding position; obtaining profile data related to the change in fluid pressure; and comparing the profile data to predetermined criteria to determine a condition of the valve.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Described herein is a medical fluid infusion system including a pump system configured to deliver a fluid drug to a patient. The system includes a pump, such as a piston pump, for driving fluid to a patient. One or more pressure sensors are configured to measure and detect changes in fluid pressure in a fluid flow line of the infusion system. The changes in fluid pressure, when detected, can be an indication of proper or improper functioning of a valve system of the pump system of the fluid infusion system.

Figure 1:
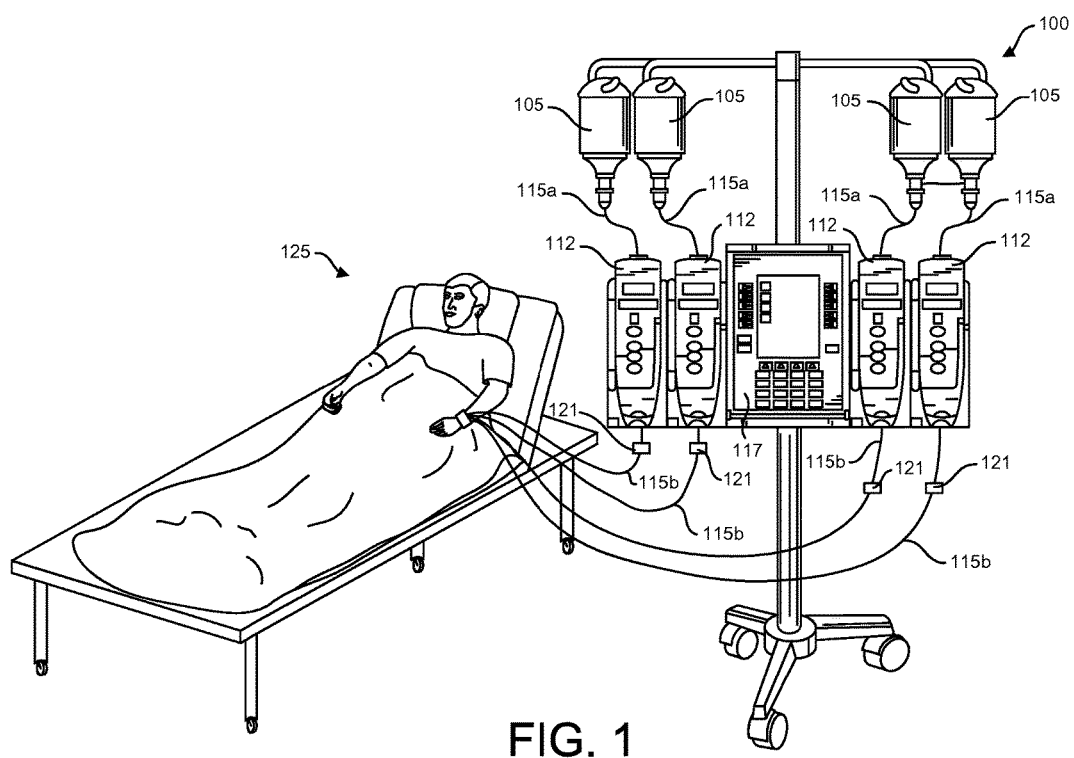
FIG. 1 is a schematic view of an infusion system according to one implementation.

FIG. 1 shows a schematic representation of a fluid infusion system 100. The fluid infusion system 100 is described herein in the context of being a bedside fluid drug infusion system for a patient although it should be appreciated that the features described herein may be used with any of a variety of fluid pumping systems and are not limited to drug infusion systems.

With reference to FIG. 1, the infusion system 100 includes one or more fluid containers, such as intravenous (IV) bags 105, each of which is fluidly coupled to a respective fluid pump device 112 via a fluid conduit, such as a fluid line 115 having a lumen for flow of fluid. The fluid container is described herein as being an IV bag although any type of fluid container is within the scope of this disclosure including for example a syringe, bottle, etc. Each IV bag 105 contains a supply of fluid (such as a liquid drug or any other fluid) to be pumped to a patient. Each pump device 112 is configured to pump fluid from a respective IV bag 105 toward a patient via a distal portion 115b of fluid line 115. The pump device 112 can be any type of pump that involves the stoppage of fluid flow including a peristaltic pump. The pump device 112 for example can be a commercially available infusion pump, such as the Alaris® Pump module (CareFusion, San Diego, Calif.) or the Plum A+™ Infusion System (Hospira, Lake Forest, Ill.) or any other infusion pump. In the illustrated embodiment, the system includes a plurality of pump devices 112 each with a corresponding IV bag 105 and fluid line 115. A central controller 117 is adapted to control one or more of the pump devices 112. It should be appreciated that the system can include any quantity of pump devices and corresponding IV bag and fluid line.

With reference still to FIG. 1, each fluid line 115 has a proximal portion 115a upstream of the pump device 112 with the proximal portion 115a fluidly coupled to the IV bag 105 such as via a drip chamber. A distal portion 115b of each fluid line 115 downstream of the corresponding pump device 112 attaches to the patient 125 via an IV connection. A pumping mechanism of each pump device 112 acts on the respective fluid line to move fluid from the IV bag 105 to the patient. The pumping mechanism of each pump device 112 can act on a fluid line or it can act on at least a portion of a removable cassette that includes a fluid conduit The pumping mechanism can vary and, for example, can be a piston pump, as described in more detail below. The fluid line 115 forms a single fluid connection that extends from the IV bag 105 to the patient or may be interconnected with a removable cassette, such as the type of cassette described in U.S. patent application Ser. No. 14/557,446 entitled "Pump Cassettes with Slider and Infusion Pump Systems" which is incorporated herein by reference, but in any event it forms a single fluid pathway from the IV bag 105 to the patient.

The fluid line 115 may be formed of a single tube or may be formed of a series of tubes removably attached to one another, such as in an end-to-end manner using any of a variety of connectors such as Luer connectors. The fluid line 115 forms a continuous fluid lumen that provides a fluid pathway from the IV bag 105 toward the patient. This continuous fluid lumen may include any of a variety of components that facilitate or otherwise are used in connecting the tubes and/or pumping fluid, including, for example, the micro infuser device described herein, valves, filters, free-flow stop valves, pressure and air detection regions or components and access connectors, etc. Any of a variety of additional components may be used, including, for example, anti-free flow devices, pressure sensing components, air detection components, etc.

Figure 2:
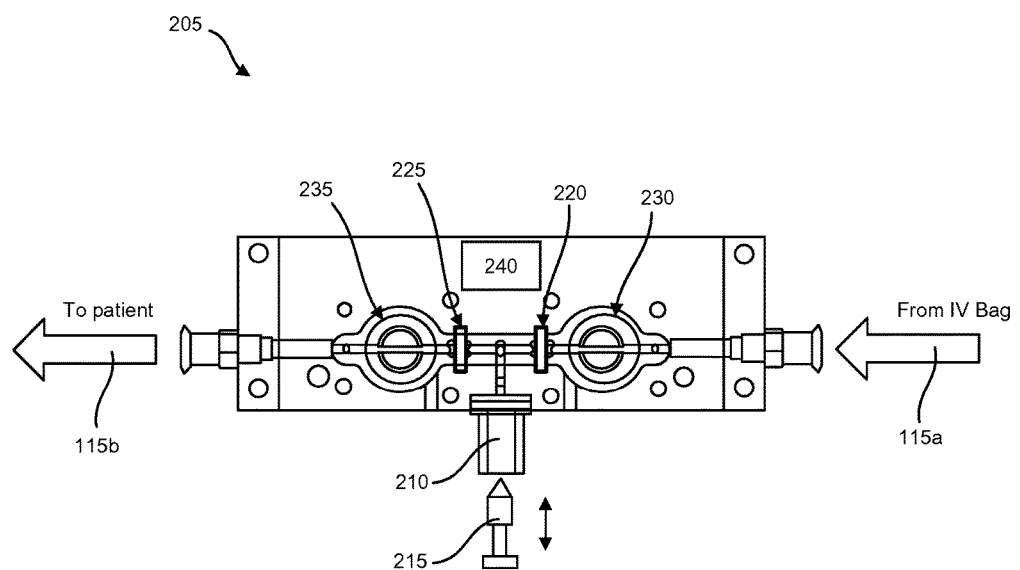
FIG. 2 is a view of a pumping mechanism of the infusion system.

FIG. 2 shows a representation of an exemplary cassette 205 that is inserted into the pump devices 112. The pumping mechanism 215 can be part of or contained within a the pump device 112. As mentioned, the pumping mechanism 215 is a piston pump. The fluid line 115 includes an upstream region 115a fluidly connected to an IV bag 105 (FIG. 1) such that fluid from the IV bag can flow into the pump mechanism. The fluid line 115 further includes a downstream region 115b that leads to the patient 125. The fluid line 115 is coupled to the cassette 215 in a manner that permits the pumping mechanism 215 to act on a piston chamber 210.

The cassette 215 includes the piston chamber 210 in which a piston 215 is movably positioned or to which the piston 215 is movably coupled. The piston chamber 210 is in fluid communication with the fluid line 115. The pumping mechanism 215 can move into and out of the piston chamber 210 or within the piston chamber 210 to generate a pressure differential that causes fluid to flow into and out of the chamber from the upstream region 115a toward the downstream region 115b of the fluid line 115. In this regard, as the pumping mechanism 215 moves downward relative to the piston chamber, fluid is drawn into the piston chamber 210 from the fluid line 115a. As the pumping mechanism 215 moves upward relative to the piston chamber 210, fluid is forced out of the piston chamber 210 into the fluid line 115b toward the patient.

With reference still to FIG. 2, the cassette 205 includes an upstream valve 220 and a downstream valve 225. The upstream valve 220 is positioned upstream of the piston chamber 205 such that it can regulate the flow of fluid into the piston chamber 205. The downstream valve 225 is positioned downstream of the piston chamber 205 such that it can regulate the flow of fluid out of the piston chamber 205 toward the patient. The valves can be any type of valves that regulate or control fluid flow through a flow pathway. For example, one of the valves may be an occlude valve and the other valve can be a check valve. Other variations are within the scope of this disclosure.

In addition, the cassette 205 includes an upstream pressure sensor 230 positioned upstream of the upstream valve 220. A downstream pressure sensor 235 is positioned downstream of the downstream valve 225. Any type of pressure sensor for measuring fluid flow pressure can be used. In an embodiment, the valves are occluder type valves that move between an open state wherein the valves permit fluid flow through a flow pathway, and a closed state that occludes fluid flow through a flow pathway. The valves are actuated by actuators that are part of the pump device 112 and that interface with the valves 225 and 220 to selectively control the flow of fluid into and out of the pump chamber 210. On the downward stroke of the pumping mechanism 215, the valve actuator interfacing with upstream valve 220 will be in a non-occluding state allowing fluid to flow from the fluid 115a and into the pump chamber 210. The valve actuator interfacing with the downstream valve 225 will be in an occluding state preventing fluid from flowing from the fluid line 115b into the pump chamber 210. On the upstroke of the pumping mechanism 215, the actuator for the upstream valve 220 will engage to an occluding position and the actuator for the downstream valve 225 will release to a non-occluding state thereby permitting fluid to flow from the pump chamber 210 to the fluid line 115b and prevent fluid from flowing from the fluid line 115a to the pump chamber 210. In FIG. 2, the upstream pressure sensor 230 is configured to measure fluid pressure in the fluid line 115a at a location adjacent or near the upstream valve 220, although the upstream pressure sensor 230 could be placed anywhere along the fluid line 115a upstream of the upstream valve 220. Likewise in FIG. 2, the downstream pressure sensor 235 is configured to measure fluid pressure in the fluid line 215b at a location adjacent or near the downstream valve 225, but the downstream pressure sensor 235 could be placed anywhere along the fluid line 115b that is downstream of the downstream valve 225. In another embodiment, a pressure sensor is positioned inside the piston chamber 210 in addition to or in place of the pressure sensors 230, 235.

The valve mechanism operates in conjunction with the piston pump as follows. With the downstream valve 225 closed and the upstream valve 220 open, the piston moves downward relative to the piston chamber 210 to create a pressure differential that draws fluid into the piston chamber from the IV bag 105 via the upstream region 115a of the fluid flow line 115. With fluid contained within the piston chamber 210, the downstream valve 225 then opens and the upstream valve 220 closes. The piston 215 then moves upward relative to the piston chamber 210 to force fluid out of the piston chamber 210 toward the patient via the downstream region 115b of the fluid flow line 115. This cycle repeats over and over to create a continuous fluid flow from an IV bag 105 toward the patient 125.

Changes in fluid pressure can be measured when one of the fluid valves 225, 220 closes and fluid flow suddenly stops across the valve that has closed. This is a result of a "water hammer" effect wherein an abrupt stop of fluid flow results in a sudden force being exerted against the valve that just closed. The water hammer effect is a pressure surge or wave caused when fluid in motion is forced to stop suddenly, such as upon the closing of the valve that occurs during the fluid flow cycle of the pumping mechanism 205. When the valve suddenly closes, the mass of water before the closure is still moving thereby building up high pressure and a resulting shockwave, resulting in a pressure spike. The value of the pressure spike will vary based upon the type of fluid and the flow rate of the fluid through the fluid line 115. For example the magnitude of the pressure spike is larger where the fluid flow rate is larger relative to lower fluid flow rates. The frequency of the pressure spike is a function of the size of the fluid line, channel compliance, and fluid density. In addition, the pressure spike may be a positive or negative pressure spike that occurs upon the opening or closing of the valve.

Information about a particular valve can be determined based upon a pressure spike profile measured at least in part by the pressure sensor at the valve when the valve closes. The pressure spike profile can include any type of information about the pressure spike including, for example, magnitude of pressure, time between the current pressure spike in the previous pressure spike, and any other information about the pressure spike occurred. The pressure spike profile may be dependent on the type of fluid, the velocity of the fluid prior to the valve closing, and additional data regarding the fluid.

Information about a particular valve can be gleaned based upon the pressure spike profile and/or a comparison of the pressure spike profile to predetermined criteria. For example, the information can relate to whether a valve is functioning properly by measuring the frequency and magnitude of the pressure spike when the valve closes and comparing the frequency and/or magnitude of the pressure spike to predetermined criteria. If the magnitude and/or frequency of the pressure spike does not meet a predetermined criteria for a particular valve where the pressure spike occurred, it can be determined, for example, that the valve where the pressure spike occurred is not functioning properly. The pressure spikes occur at or near the time when a valve is actuated. Given that valve actuation occurs at specific and/or expected times, it can be determined that an error has occurred (i.e., the valve is malfunctioning) if the pressure spike does not occur at the expected time. Or, if a pressure spike occurs repeatedly at an encoder position or time that does not correlate to a valve actuation or movement, it can be determined that the timing of a valve is off. In addition, it is likely that if the timing of the valves is off, an incorrect flow rate is being delivered to the patient.

In an embodiment, each of the pressure sensors 230 and 235 is coupled to a computer processor 240 that includes software configured to evaluate a pressure spike measured by one of the valves, and compare the pressure spike to predetermined criteria such as criteria that is indicative of whether the pressure spike is functioning properly. If the pressure spike does not meet predetermined criteria, the microprocessor 240 may activate a signal, which can be an audio, visual, or a tactile signal, wherein the signal indicates to a user that one of the valves is not operating properly based upon the comparison of the pressure spike to the predetermined criteria. The microprocessor may also send a signal to a remote location or to a remote server, where the signal may be recorded or other action may be taken. For example, the pressure spike may indicate that the valve actuators are broken, that the valves themselves are broken or that the valves are operating pursuant to an incorrect timing.

In another example, an abnormally small pressure spike or the lack of a pressure spike may indicate that the valve is broken, that there is an incorrect flow rate, or that a free flow condition is present.

In a method of use, the pump mechanism 215 is operating to cause fluid flow from the upstream region 115a toward the downstream region 115b and toward a patient. As mentioned, the fluid flow through the fluid line 115 occurs as a result of the pump mechanism 215 moving up and down through the piston chamber 210 in combination with a corresponding opening and closing of the valves 220 and 225. When one of the valves closes, a pressure spike is measured by the corresponding pressure sensor. A pressure spike profile based on data measured by the pressure sensor is communicated to the computer processor 240, which then evaluates the pressure spike by comparing its pressure spike profile to predetermined criteria. If it is determined that, based on the comparison, the pressure spike does not meet predetermined criteria then the computer processor sends a signal to indicate to a user that a certain valve condition exists such as that one of the valves is malfunctioning.

It should also be appreciated that the described infusion systems are not limited to intravenous infusions, but can be used for any number of infusion types to a patient through a catheter including but not limited to parenteral, intraarterial, intracardiac, intraosseous, intramuscular, intrathecal, intraperitoneal, epidural, intracerebral, gastrointestinal, and the like. In addition, the infusion systems described herein can be used in conjunction with any of a variety of electronic and/or software medication management systems, such as the system described in U.S. Patent Publication 2011/0060758 to Schlotterbeck. U.S. Patent Publication 2011/0060758 is incorporated herein by reference in its entirety.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A fluid infusion system for delivery of a fluid medicant to a patient, comprising:
 a fluid line through which fluid flows toward the patient;
 a first valve configured to be positioned within a pump located along the fluid line, wherein the first valve opens to permit fluid flow through the fluid line and closes to prohibit fluid flow through the fluid line;
 a first pressure sensor positioned along the fluid line, wherein the first pressure sensor measures fluid pressure at a location in the fluid line adjacent the first valve;
 a processor coupled to the first pressure sensor, wherein the processor is configured to detect an occurrence of a first fluid pressure spike and a second fluid pressure spike at the first valve, and wherein the processor is configured to compare timing data between the first fluid pressure spike and the second fluid pressure spike in order to determine whether the first valve is functioning properly, and wherein the processor emits a signal indicative of whether the first valve is functioning properly.

2. The fluid infusion system as in claim 1, further comprising an indicator that indicates to a user that the processor has emitted the signal.

3. The fluid infusion system as in claim 2 wherein the indicator is at least one of an audio, visual, and tactile, indicator.

4. The fluid infusion system as in claim 1, further comprising the pump.

5. The fluid infusion system as in claim 4, wherein the pump is a piston pump.

6. The fluid infusion system as in claim 1, further comprising a second valve positioned along the fluid line downstream of the first valve, wherein the second valve opens to permit fluid flow through the fluid line and closes to prevent fluid flow through the fluid line.

7. The fluid infusion system as in claim 6, further comprising a second pressure sensor positioned along the fluid line, wherein the second pressure sensor measures fluid pressure at a location in the fluid line adjacent the second valve.

8. The fluid infusion system as in claim 7, wherein the second pressure sensor is positioned downstream of the second valve.

9. The fluid infusion system as in claim 1, further comprising:
a second valve positioned along the fluid line downstream of the first valve, wherein the second valve opens to permit fluid flow through the fluid line and closes to prevent fluid flow through the fluid line;
a second pressure sensor positioned along the fluid line, wherein the second pressure sensor measures fluid pressure at a location in the fluid line adjacent the second valve;
the pump positioned along the fluid line between the first valve and the second valve.

10. The fluid infusion system as in claim 9, wherein the pump is a piston pump.

11. The fluid infusion system as in claim 1, wherein the processor emits the signal to a user.

12. The fluid infusion system as in claim 1, wherein the signal is at least one of an audio, visual, and tactile signal.

13. The fluid infusion system as in claim 1, wherein the processor sends the signal to at least one of a server and a remote location.

14. The fluid infusion system as in claim 1, wherein the timing data relates to a time between the first pressure spike and the second pressure spike.

15. The fluid infusion system as in claim 1, wherein the timing data relates to an expected time of at least one of the first pressure spike and the second pressure spike.

16. A method of detecting a condition of a valve system in a fluid infusion system with a valve actuator that moves from occluding to non-occluding positions, comprising:
using a processor coupled to a pressure sensor to detect a change in fluid pressure that occurs in the fluid line at the valve system when the valve actuator moves from a non-occluding position to an occluding position, the change in pressure resulting in a pressure spike at the valve system;
using the processor to obtain profile data related to the change in fluid pressure, the profile date relating to an expected time at which the pressure spike should occur; and
using the processor to determine that a valve associated with the valve actuator has malfunctioned based upon the pressure spike not occurring at an expected time.

17. The method as in claim 16, wherein the profile data includes a magnitude of the pressure spike.

18. The method as in claim 16, wherein the profile data includes a frequency of the pressure spike.

19. The method as in claim 16, further comprising providing an indication as to the condition of the valve associated with the valve actuator.

20. The method as in claim 19, wherein the indication is at least one of an audio, visual, and tactile indication.

21. The method as in claim 16, wherein the pressure spike occurs immediately after the valve opening or closing.

* * * * *